United States Patent
Voigt et al.

(10) Patent No.: US 8,812,431 B2
(45) Date of Patent: Aug. 19, 2014

(54) METHOD AND SYSTEM FOR MEDICAL DECISION SUPPORT USING ORGAN MODELS AND LEARNING BASED DISCRIMINATIVE DISTANCE FUNCTIONS

(75) Inventors: Ingmar Voigt, Erlangen (DE); Dime Vitanovski, Erlangen (DE); Razvan Ioan Ionasec, Lawrenceville, NJ (US); Alexey Tsymbal, Erlangen (DE); Bogdan Georgescu, Plainsboro, NJ (US); Shaohua Kevin Zhou, Plainsboro, NJ (US); Martin Huber, Uttenreuth (DE); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 540 days.

(21) Appl. No.: 13/016,259

(22) Filed: Jan. 28, 2011

(65) Prior Publication Data
US 2011/0191283 A1    Aug. 4, 2011

Related U.S. Application Data

(60) Provisional application No. 61/300,924, filed on Feb. 3, 2010.

(51) Int. Cl.
| | |
|---|---|
| *G06F 17/30* | (2006.01) |
| *G06F 19/12* | (2011.01) |
| *G06F 19/26* | (2011.01) |
| *A61B 5/05* | (2006.01) |
| *G06N 5/00* | (2006.01) |
| *G06G 7/60* | (2006.01) |

(52) U.S. Cl.
CPC ... *G06G 7/60* (2013.01); *G06N 5/00* (2013.01)
USPC .............................. 706/54; 600/416; 706/20

(58) Field of Classification Search
USPC ........................................... 706/54
See application file for complete search history.

(56) References Cited

U.S. PATENT DOCUMENTS

| | | |
|---|---|---|
| 6,598,307 B2 | 7/2003 | Love et al. |
| 2005/0281447 A1 | 12/2005 | Moreau-Gobard et al. |
| 2008/0085043 A1 | 4/2008 | Watanabe et al. |
| 2009/0154785 A1 | 6/2009 | Lynch et al. |
| 2010/0239147 A1 | 9/2010 | Vitanovski et al. |

OTHER PUBLICATIONS

Ionasec et al. (Ionasec), Personalized Modeling and Assessment of the Aortic-Mitral Coupling from 4D TEE and CT, 2009.*

(Continued)

*Primary Examiner* — Jeffrey A Gaffin
*Assistant Examiner* — Nathan Brown, Jr.

(57) ABSTRACT

A method and system for providing medical decision support based on virtual organ models and learning based discriminative distance functions is disclosed. A patient-specific virtual organ model is generated from medical image data of a patient. One or more similar organ models to the patient-specific organ model are retrieved from a plurality of previously stored virtual organ models using a learned discriminative distance function. The patient-specific valve model can be classified into a first class or a second class based on the previously stored organ models determined to be similar to the patient-specific organ model.

29 Claims, 5 Drawing Sheets

(56) References Cited

OTHER PUBLICATIONS

Richard A. Robb et al., Patient-Specific Anatomic Models From Three Dimensional Medical Image Data for Clinical Applications in Surgery and Endoscopy. Journal of Digital Imaging, vol. 10, No. 3, Suppl. 1, pp. 31-35 [online], Aug. 1997 [retrieved on Feb. 18, 2014]. Retrieved from the Internet:<URL:http://link.springer.com/article/10.1007%2FBF031>.*

Frank Moosmann et al., Randomized Clustering Forests for Image Classification, IEEE Transactions on Pattern Analysis and Machine Intelligence, vol. 30, No. 9 [online], Sep. 2008 [retrieved on Feb. 18, 2014]. Retrieved from the Internet:<URL:http://ieeexplore.ieee.org/xpls/abs_all.jsp?arnumber=4384498&tag=1>.*

Ionasec, et al., "Personalized Modeling and Assessment of the Aortic-Mitral Coupling from 4D TEE and CT", in International Conference on Medical Imaging Computing and Computer-Assisted Intervention (MICCAI), Sep. 2009.

Calleja, et al., "Automated Quantitative Modeling of the Aortic Valve and the Root in Aortic Regurgitation Using Valumetric 3-D Tranesophageal Echocardiography", J. Am. Coll. Cardiol., 2010.

Schievano, et al., "Variations in Right Ventricular Outflow Tract Morphology following Repair of Congenital Heart Disease: Implications for Percutaneous Pulmonary Valve Implantation", Journal of Cardiovascular Magnetic Resonance 9(4) 2007, pp. 687-695.

* cited by examiner

METHOD AND SYSTEM FOR MEDICAL DECISION SUPPORT USING ORGAN MODELS AND LEARNING BASED DISCRIMINATIVE DISTANCE FUNCTIONS

This application claims the benefit of U.S. Provisional Application No. 61/300,924, filed Feb. 3, 2010, the disclosure of which is herein incorporated by reference.

BACKGROUND OF THE INVENTION

The present invention relates to model based decision support, and more particularly, to decision support using organ models estimated from medical image data and learning based discriminative distance functions.

Valvular heart disease (VHD) is a cardiac disorder that affects a large number of patients and often requires elaborate diagnostic procedures, intervention, and long-term management. Abnormalities may occur in conjunction with other heart diseases, and can be caused by congenital defects, pulmonary hypertension, endocarditis, rheumatic fever, and carcinoid heart disease. Such conditions require constant monitoring and a complex clinical workflow, including patient evaluation, percutaneous intervention planning, valve replacement and repair, and follow-up evaluations.

Treatment of VHD is typically expensive and conventional VHD treatment has a relatively high in-hospital death rate due to elaborate, time consuming, and potentially inaccurate diagnostic procedures and complex interventions into patients' cardiac systems. Recent advances in medical imaging technology have enabled 4D imaging with computed tomography (CT) and ultrasound. However, due to lack of efficient and convenient tools, anatomical performance assessment of the cardiac valves typically relies on manual measurements in 2D image planes derived from the 4D image acquisitions. Although such performance assessment can be error prone and time consuming, diagnosis, treatment decisions, interventional planning, and follow up evaluation typically rely on such performance assessment, which can lead to suboptimal treatment results, follow up interventions, and increased treatment costs. Moreover, clinical decisions are based on generic information from clinical guidelines and publications and personal experience of clinicians. Clinical decisions are not necessarily personalized to the specific patient, due to the potential lack of similar cases, which would provide patient histories and treatment results as references for decision support.

BRIEF SUMMARY OF THE INVENTION

The present invention provides a method and system for medical decision support using learning based discriminative distance functions and virtual organ models derived from medical image data. Embodiments of the present invention derive high-level information from organ models and extracted features using learning based discriminative distance functions and utilize relative neighborhood graphs to visualize the relationships between various cases. Embodiments of the present invention are flexible and allow similarity between cases to be arbitrarily defined and learned based on any meaningful concept.

In one embodiment of the present invention, a virtual patient-specific organ model is generated from medical image data of a patient. One or more similar organ models to the patient-specific organ model are retrieved from a plurality of previously stored organ models using a learned discriminative distance function. The learned discriminative distance function can be trained based on various representations and learning algorithms, such as equivalence constraints assigned to the training data using one of Random Forests and a boosting algorithm or the intrinsic Random Forest distance. The patient-specific organ model can be classified into one of a first class and a second class based on the retrieved one or more organ models similar to the patient-specific organ model. The patient specific organ model may be a patient-specific heart valve model generated from 4D cardiac image data.

These and other advantages of the invention will be apparent to those of ordinary skill in the art by reference to the following detailed description and the accompanying drawings.

DETAILED DESCRIPTION

The present invention relates to image based organ classification using learning based discriminative distance functions for model-based decision support. Embodiments of the present invention are described herein to give a visual understanding of various organ classification methods. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. While embodiments of the present invention described herein exemplify applications to heart valve disease, the method and system is not limited thereto and may be similarly used for other organs and in any other context where organ morphology and motion patterns encode application specific concepts, such as pathology or treatment suitability.

Case-based reasoning (CBR) systems are an important subgroup of clinical decision support systems and provide a way to retrieve similar cases and related clinical data, such as diagnoses, treatment decisions, follow up results, and long term outcomes. Embodiments of the present invention provide CBR systems for classifying a patient's organ by determining similarity to previous data from a different patient. The present inventors have recognized that, in order to develop an effective CBR for medical decision support based on organ models, it is important to define a meaningful distance function which can handle the complexity of clinical data and a transparent way to visualize the underlying inter-patient similarity.

Embodiments of the present invention provide a generic method for deriving high-level information from virtual (in silico) organ models, which capture its morphology and function, and derived features using learning based discriminative distance functions. Neighborhood graphs are used to visualize the relationships among cases determined using the learned discriminative distance functions. The learning based discriminative distance functions described herein provide flexibility for arbitrarily defining and learning similarity among organs based any meaningful concept. Such discriminative distance functions are, for example, applied to physiological models of heart valves, which cover the complete morphology of the heart valves and can be modeled from 4D cardiac computed tomography, 4D transesophageal ultrasound, and 3D isotropic magnetic resonance (MR) images. Embodiments of the present invention can be applied to various clinically relevant applications including, but not limited to, diagnosis of diseased and healthy valves, percutaneous pulmonary valve implantation (PPVI) planning, and definition of personal treatment targets.

Figure 1:
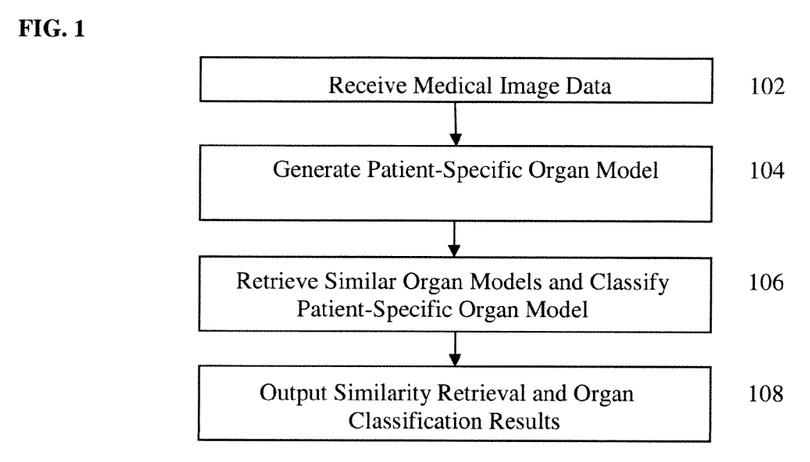
FIG. 1 illustrates a method for providing valvular heart disease decision support using a discriminative distance function according to an embodiment of the present invention.

FIG. 1 illustrates a method for providing valvular heart disease decision support using a discriminative distance function according to an embodiment of the present invention. The method of FIG. 1 can be applied to various clinically relevant applications to provide decision support for diagnosis and treatment of valvular heart disease.

Referring to FIG. 1, at step 102, medical image data is received. For example, in the context of VHD, the medical image data can be 4D cardiac CT data, but the present invention is not limited thereto. For example, ultrasound data and MRI data can also be used to generate a patient specific pulmonary trunk model. The 4D CT data can be a dynamic sequence of 3D cardiac CT volumes taken over a period of time. Each 3D CT volume in the sequence can be referred to as a frame. The sequence of CT volumes can be taken over at least one full cardiac cycle. It is possible that the image data can be received directly from an image acquisition device, such as a CT scanning device, in real time as the image data is acquired by the image acquisition device. It is also possible that the image data can be received by loading image data stored in a memory or storage of a computer system, or some other computer readable medium.

At step 104, a virtual patient-specific organ model is generated from the medical image data. For example, in the context of valvular heart disease decision support, a 4D patient specific heart valve model is generated from the 4D cardiac image data. In particular, the morphology and dynamics of the aortic-mitral complex and/or the pulmonary trunk are represented by 4D physiologically compliant models estimated from the 4D cardiac data for a patient. For example, a patient specific model of the aortic-mitral complex can be detected from the 4D image data as described in Ionasec, et al., "Personalized Modeling and Assessment of the Aortic-Mitral Coupling from 4D TEE and CT" in International Conference on Medical Imaging Computing and Computer-Assisted Intervention (MICCAI), September 2009, which is incorporated herein by reference, and a patient-specific model of the pulmonary trunk can be detected from the 4D image data as described in Vitanovski, et al., "Personalized Pulmonary Trunk Modeling for Intervention Planning and Valve Assessment Estimated from CT Data" in International Conference on Medical Imaging Computing and Computer-Assisted Intervention (MICCAO, September 2009, which is incorporated herein by reference.

In order to generate the patient specific models of the aortic-mitral complex and the pulmonary trunk, a generic anatomic model is fit to the image data. The central anatomical structures of the aortic root and leaflets, the mitral leaflets, and the pulmonary trunk are represented by Non-uniform rational B-Splines (NURBS) and a set of clinically relevant anatomical landmarks which constrain them topologically and geometrically to capture the large morphological and pathological variation between patients.

The model estimation can be performed in an automatic and hierarchical fashion by applying robust discriminative learning and incremental searching techniques at each step, allowing for manual correction if desired by the user. These steps include model estimate of the piecewise affine rigid transformation, landmark detection, followed by centerline detection for the pulmonary trunk, and final boundary fitting. For each stage i a discriminative classifier $H_i$ is trained using a probabilistic boosting tree (PBT) in combination with Haar-like and/or steerable features. $H_i$ then used to incrementally scan the search space of the acquired image I to determine the parameters $\hat{\theta}_i$ with maximum probability:

$$\hat{\theta}_i = \underset{\theta_i \in \Theta_i}{\mathrm{argmax}}(p(\theta_i \mid I) = H_i(\theta_i \mid I)). \tag{1}$$

Figure 2:
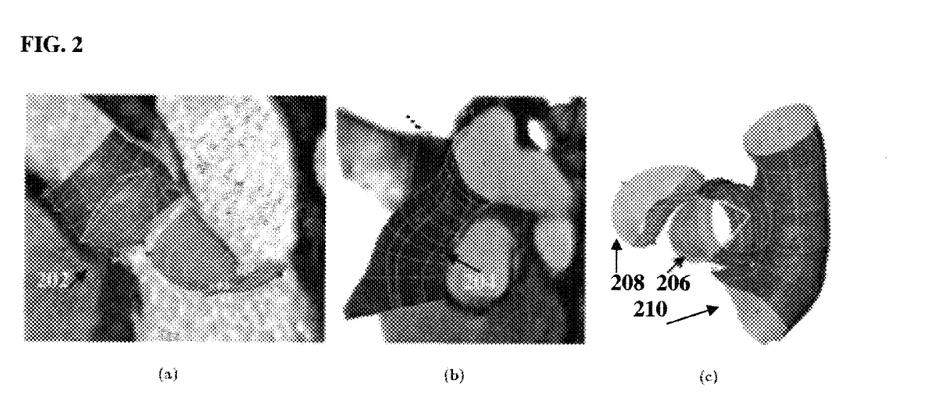
FIG. 2 illustrates exemplary patient specific valve models estimated from 4D cardiac image data.

The results of each stage are propagated to subsequent stages in order to initialize and constrain the search spaces of the successive estimation problems, by piecewise rigid and non-rigid transformations. In order to address the problem of temporally varying appearances and image characteristics, the temporal coherence can be exploited by incrementally learning and estimating landmark trajectories in the Fourier space and using ISOMAP motion models to predict the shape deformation over time. FIG. 2 illustrates exemplary patient specific valve models estimated from 4D cardiac image data. As shown in FIG. 2, image (a) shows a model 202 of the aortic-mitral complex and image (b) shows a model 204 of the pulmonary trunk. Image (c) shows models for the aortic valve 206, mitral valve 208, and pulmonary trunk 210 visualized together.

Figure 3:
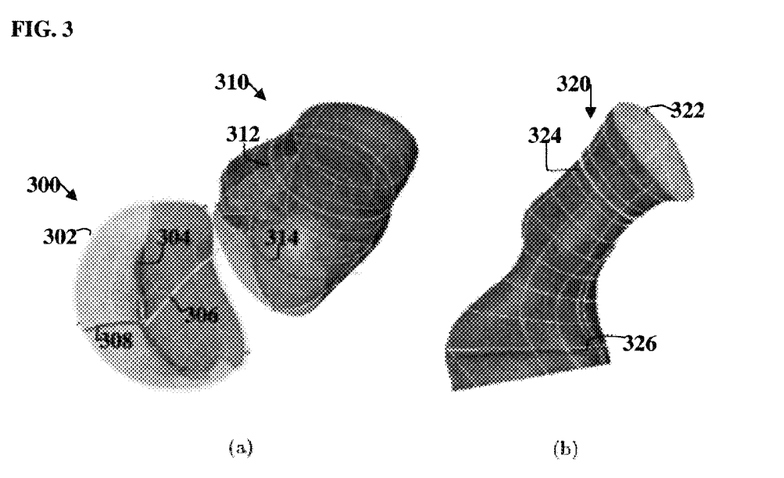
FIG. 3 illustrates various measurements calculated from patient specific valve models.

Clinically established measurements characterizing the valves' morphology and the severity of various diseases can be derived from the valve models in a straightforward manner by fast and simple geometric computations, such as diameters, annular and valvular areas, inter-landmark distances, angles based on clinical observation and research. FIG. 3 illustrates various measurements calculated from patient specific valve models. As illustrated in FIG. 3, image (a) shows a mitral valve model 300 and an aortic valve model 310. The mitral valve model 300 shows the following measurements: mitral annular circumference and area (302), mitral valve orifice and closure line length (304), mitral anterior leaflet length (306), and mitral posterior leaflet length (308). The aortic valve model 310 shows the following measurements: aortic sinotubular junction diameter and are (312) and aortic sinuses of valsava diameter and area (314). Image (b) shows a pulmonary valve model 320 and measurements pulmonary trunk diameter at bifurcation (322), pulmonary trunk minimal diameter (324), and pulmonary trunk maximal diameter (326). Various valve measurements are further described in Calleja, et al., "Automated Quantitative Modeling of the Aortic Valve and The Root in Aortic Regurgitation Using Volumetric 3-D Tranesophageal Echocardiography", *J. Am. Coll. Cardiol.* 2010, which is incorporated herein by reference. It is to be understood that the above examples of clinical measurements are not intended to limit the present invention and various other clinical measurements may also be derived from the patient-specific organ models.

The shape S of the valve model is represented by a discrete set of N 3D points $P_i$ from the NURBS surfaces $S_i$:

$$S=\{P_i=(P_i^x, P_i^y, P_i^z) | P_i = S_i(u,v); u,v \in [0;1]\}, \quad (2)$$

According to an exemplary implementation, in order to achieve an accurate representation, 951 discrete points can be sampled from the aortic valve surfaces all together, while the pulmonary trunk can be represented by 2000 points.

Returning to FIG. 1, at step 106, similar organ models are retrieved from a database with cases of previously examined patients and the patient specific organ model is classified using a learned discriminative distance function. For example, in the context of valvular heart disease, similar valve models to the patient-specific heart valve model are retrieved from a plurality of previously stored valve models. Step 106 of FIG. 1 addresses two tasks: identification and retrieval of similar cases to the organ model, which measures the similarity of the organ model and previously stored organ models, and a binary classification problem based on the geometric valve model and derived features, such as various measurements derived from the geometric organ model. According to an embodiment of the present invention, the second task (binary classification) can be formulated using the first task (similarity measurement to previous cases). Accordingly, instead of learning a classifier directly, discriminative distance functions are trained to estimate a "distance" which measures the similarity between a pair of cases (e.g., a valve model and a previously stored valve model), and the learning process is divided into two sequential steps, i.e., distance learning followed by classification or clustering, where each step requires a search in a less complex functional space than direct learning of a classifier.

The labels for classification $y \in \{-1,+1\}$ are chosen depending on the application. For example, the labels can correspond to the classifications of unsuitable patient data and suitable patient data for PPVI or to the classifications or healthy and diseased patient data. To learn the distance function, each case in a set of previously stored annotated training data is represented with a parameter vector C containing the N 3D points $P_i$ of the respective pulmonary trunk model and a set of M additional features F, derived from the model, such that:

$$\hat{y} = \underset{y \in \{-1,+1\}}{\operatorname{argmax}}(p(y|C)) \quad (3)$$
$$C = ((P_1^x, P_1^y, P_1^z), \ldots, (P_N^x, P_N^y, P_N^z), F_1, \ldots, F_M)$$

Learning a distance function helps to combine the power of strong learners with the transparency of nearest neighbor classification. Moreover, learning a proper distance function can be especially helpful for high dimensional data with many correlated, weakly relevant and irrelevant features, where most traditional techniques would fail. Further, choosing an optimal distance function can make classifier learning redundant.

According to an advantageous implementation, the discriminative distance function can be learned using equivalence constraints. Learning from weak representations, such as equivalence constraints, provides high flexibility for learning arbitrary functions. Equivalence constraints are represented using triplets $(C^1, C^2, y)$, where $C^1$ and $C^2$ are organ model parameters in the original space and $y \in \{-1,+1\}$ is a label indicating whether the two organ model instances are similar (from the same class or cluster) or dissimilar. Learning from such triplets is referred to as learning in the product space (i.e., with pairs of points as inputs). An alternative to learning in the product space is learning in the difference space, i.e., the space of vector differences. Commonly, a binary distance function is output from learning from equivalence constraints, predicting only whether two objects are similar to each other. This can be overcome by using the signed margin of margin-based classifiers such as SVM and boosting as the required distance function. According to an embodiment of the present invention, a signed margin of a model constructed using a Random Forest (RF) can be used as the required distance function for distance learning from equivalence constraints. According to an alternate embodiment, a signed margin of a model constructed using a boosting algorithm, such as Adaboost, can be used as the require distance function for learning from the equivalence constraints.

For an RF learned for a certain classification problem, the proportion of trees where two instances appear together in the same leaves can be used as a measure of similarity between them. For a given forest f, the similarity between two instances $C^1$ and $C^2$ is calculated as follows. The instances are propagated down all K trees within f and their terminal positions z in each of the trees ($z_1 = (z_{11}, \ldots, z_{1K})$ for $C^1$, similarly $z_2$ for $C^2$) are recorded. The similarity between the two instances is then equal to:

$$S(C^1, C^2) = \frac{1}{K}\sum_{i=1}^{K} I(z_{1i} = z_{2i}) \quad (4)$$

where I is the indicator function.

Accordingly, as described above, the discriminative distance function can be learned using equivalence constraints, can comprise the intrinsic random forest similarity of a Random Forest trained in the original space, or can be constructed from a combination of both.

The discriminative distance function that is learned based on the annotated training data is used to measure similarity of the organ model generated at step 104 with each of multiple previously stored cases that are, for example, maintained in a database. The learned discriminative distance function calculates a similarity score for the current patient-specific organ model and each previously stored case. This allows the most similar previous cases to the current organ model to be retrieved. The current patient-specific organ model can then be classified based on the classification of the most similar previous cases. For example, in one possible implementation, the current organ model can be clustered with the most similar previous cases to assign a classification of the most similar cases to the current organ mode. The particular classification of the organ model is dependent on the application for which the organ model is being classified.

At step 108, similarity detection and organ classification results are output. The similarity detection results can be output by displaying the previously stored cases which are detected as being most similar to the patient-patient specific organ model. This allows doctors to access patient data and patient history, as well as treatment results for the similar previously stored cases. The classification label which is used to classify the organ model can also be output. This way the doctor can make a personalized decision based on the data and treatment results that were observed in other similar cases, rather than having to rely only on generic clinical guidelines, publications, and personal experience.

According to an advantageous embodiment, the similarity detection and valve classification results can be output by visualizing the results in a relative neighborhood graph (RNG). Neighborhood graphs provide an intuitive way of patient similarity visualization with an entity-relationship representation. In a RNG, two vertices corresponding to two instances $C^1$ and $C^2$ in a data set are connected with an edge, if there is no other instance $C^3$ which is closer to both $C^1$ and $C^2$ with respect to the learned discriminative distance function $d:^3$. This can be expressed as:

$$\forall C^3 : d(C^1, C^2) \leq \max\{d(C^1, C^3), d(C^2, C^3)\}. \tag{5}$$

This RNG visualization is advantageous in that it is always planar or close to planar and connected, while nodes have a reasonable small degree, in contrast to techniques such as directed nearest neighbor or distance threshold graphs. Further, an RNG visualization has an intuitive node-link representation and is easier to read that well known heatmaps. Furthermore, according to an advantageous embodiment, additional features may be visualized with the RNG, such as visualizing image thumbnails and patient data of the nodes. The RNG visualization also has a flexible layout that can be configured to naturally visualize clusters, enlarge nodes, and filter out a set of nodes and edges.

Figure 4:
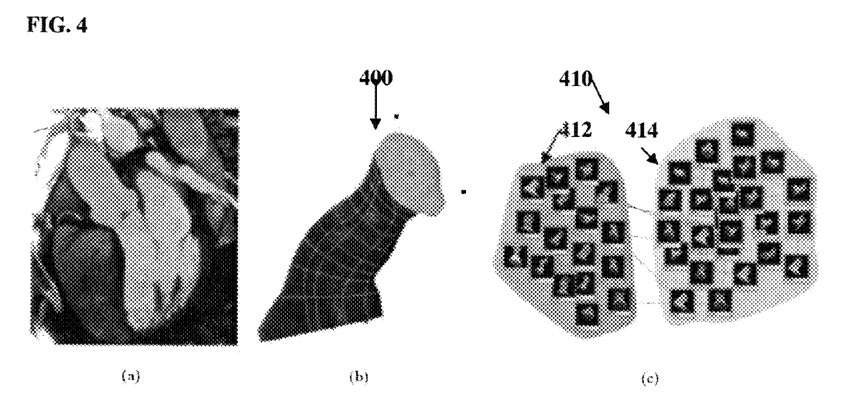
FIG. 4 illustrates an exemplary workflow and results of the method of FIG. 1 for a PPVI intervention planning application.

FIG. 4 illustrates exemplary results of the method of FIG. 1 for a PPVI intervention planning application. As illustrated in FIG. 4, image (a) shows a 3D volume from 4D CT cardiac image data acquired at step 102. Image (b) shows a personalized pulmonary trunk model 400 generated at step 104 from the 4D cardiac image data. Image (c) shows a neighborhood graph 410 generated using the learned discriminative distance function (step 106) and displayed to a user (step 108). The neighborhood graph of image (c) shows clustering based classification of pulmonary trunk models as suitable or unsuitable for PPVI. Cluster 412 corresponds to pulmonary trunks that are unsuitable for PPVI and cluster 414 corresponds to pulmonary trunks that are suitable for PPVI. The neighborhood graph 412 clearly visualizes which other cases are similar to the current valve model, which allows the user to inspect the similar valves and patient records to find diagnostic or treatment decisions. As shown in image (c) of FIG. 4, image thumbnails may be visualized for each case, which allows for easily identifying the different cases and their shape characteristics. From the graph 412, one may easily comprehend patient distribution according to the learned similarity distance function and see patient groupings, identify outliers, identify easy to classify cases, and identify borderline cases for which classification is likely to be uncertain.

As described above, shape similarity can be defined arbitrarily and depending on the application. According to various embodiments of the present invention, shape similarity can be defined and exploited differently for the following different applications for clinical decision support using organ models. It is to be understood that the following applications are not intended to limit the present invention and the above described method may also be utilized for other applications for clinical decision support based on organ models, where organ morphology and motion patterns encode application specific concepts.

Figure 5:
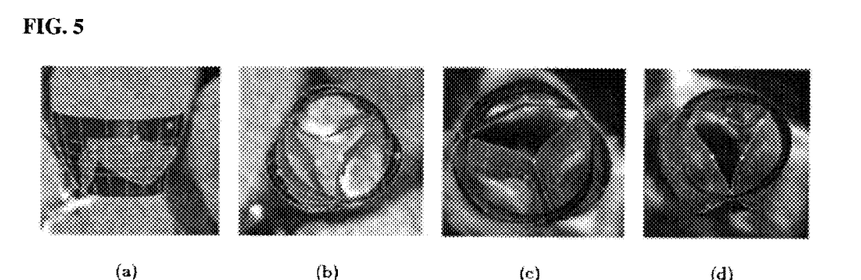
FIG. 5 illustrates exemplary pathological aortic valves in CT and ultrasound images.

One possible application for the above described method is model-driven diagnosis which classifies heart valve models into diseased and healthy cases. In this application, a learned discriminative distance function is used to retrieve similar cases to a current patient-specific valve model. The current patient-specific valve model is then classified as healthy or diseased based on the similar cases. There are two main types of heart valve malfunction: stenosis and regurgitation. Valvular stenosis is defined as an obstruction of the blood flow caused by narrowing, stiffening, thickening, fusion, or blockage of one or more valves. Valvular regurgitation is a condition in which blood leaks back in the wrong direction because the affected valve is not closing properly. Both disorders can greatly interfere with the heart's function to pump an adequate amount of blood, causing serious health problems. FIG. 5 illustrates exemplary pathological (diseased) aortic valves in CT and ultrasound images. As illustrated in FIG. 5, image (a) shows a dilated aortic valve, image (b) shows an aortic valve suffering from stenotic calcification, image (c) shows a bicuspid aortic valve, and image (d) shows an aortic valve suffering from moderate stenosis.

The classification of a valve model as healthy or diseased can be performed using a clustered RNG, generated with the underlying learning based distance measure for the input valve models. The resulting graph displays two regions indicating healthy and diseased cases, as well as the mutual similarity among the cases. Clinically established geometrical measurements can be used to determine the severity of disease and required interventions, and can be easily derived from the models to further enrich the feature pool and strengthen the classification. Accordingly, the classification may further classify a specific type of valvular heart disease and/or a severity of the disease.

Another possible application for the above described method is for interventional planning in PPVI. In particular, a patient-specific pulmonary valve model can be classified as suitable or not suitable for PPVI based on the similar cases retrieved for the patient-specific pulmonary valve model. PPVI is an alternative to traditional pulmonary valve replacement done by open heart surgery. The morphology of the pulmonary trunk is a major determinant of suitability for PPVI, as a valve stent placed in patients with pyramidal shaped pulmonary trunks has a high probability of proximal device dislodgement.

Figure 6:
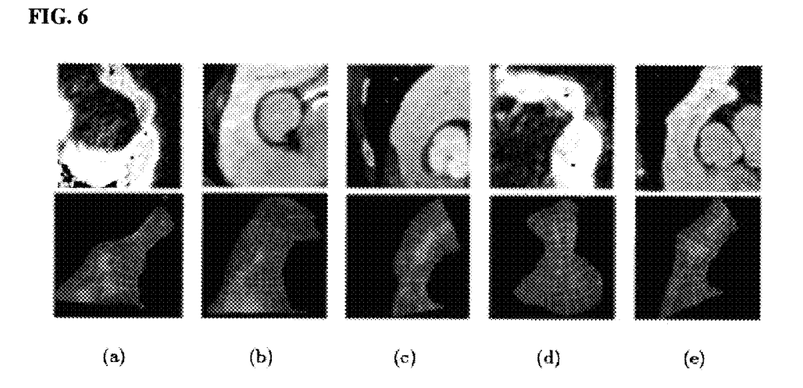
FIG. 6 illustrates various types of pulmonary trunk morphologies.

Schievano, et al., "Variations in Right Ventricular Outflow Tract Morphology Following Repair of Congenital Heart Disease: Implications for Percutaneous Pulmonary Valve Implantation", Journal of Cardiovascular Magnetic Resonance 9(4) 2007, pgs. 687-95, which is incorporated herein by reference, proposes the classification of various morphologies of the pulmonary trunk into five groups: pyramidal shape (type I), constant diameter (type II), inverted pyramidal shape (type III), wide centrally but narrowed proximally and distally (type IV), and narrowed centrally but wide proximally and distally (type V). Patients having pulmonary trunk morphology of type I are considered to be unsuitable for PPVI due to a narrow artery and high probability of device migration. Thus, in order to determine if a patient is suitable for PPVI, the classification must discriminate anatomies of type I from other classes. FIG. 6 illustrates the various types of pulmonary trunk morphologies. Image (a) of FIG. 6 shows image data and a pulmonary trunk model for a pulmonary trunk having a pyramidal shape (type I). Image (b) of FIG. 6 shows image data and a pulmonary trunk model for a pulmonary trunk having a constant diameter (type II). Image (c) of FIG. 6 shows image data and a pulmonary trunk model for a pulmonary trunk having an inverted pyramidal shape (type III). Image (d) of FIG. 6 shows image data and a pulmonary trunk model for a pulmonary trunk that is narrowed centrally but wide proximally and distally (type IV). Image (e) of FIG. 6 shows image data and a pulmonary trunk model for a pulmonary trunk that is wide centrally but narrowed proximally and distally (type V).

A trained discriminative distance function uses the features extracted from the patient specific pulmonary trunk model to cluster the patient specific pulmonary trunk model with similar pulmonary trunk models in the training data. The pulmonary trunk is classified as suitable for PPVI if the patient specific model is clustered with training examples that are suitable for PPVI (i.e., types II, III, IV, and V) and is classified as unsuitable for PPVI if the patient specific model is clustered with training examples that are not suitable for PPVI (i.e., type I). Image (c) of FIG. 5, shows a neighborhood graph 410 that clusters pulmonary trunk models into a cluster 412 corresponding to pulmonary trunks that are unsuitable for PPVI and cluster 414 corresponds to pulmonary trunks that are suitable for PPVI.

Another possible application for the above described method is retrieval similar cases for defining personalized treatment targets. The coupling of the aortic and mitral valve annuli through fibrous tissue is evident and leads to strong functional and morphological interdependency. According to an embodiment of the present invention, this mutual morphological correlation among different valves can be exploited for retrieval of similar healthy valves for a diseased case in order to define precise personalized targets of an intervention. For example, in a case of a patient with a diseased mitral valve affected by annular dilation and a healthy aortic valve, the discriminative distance function can be trained to retrieve a case with a similar healthy aortic valve and a healthy mitral valve. The healthy aortic valve of the retrieved case can be used to determine the annular dimensions of the formerly healthy mitral valve for mitral annuloplasty. In this case, the system provides to the surgeon a suggestion of which dimension of the prosthesis would actually be the best fit, such that the surgeon has an additional statistically based decision support, rather than having to rely only on generic clinical guidelines, publications, and personal experience. Furthermore, the patient-specific personalized treatment target from the retrieved similar case can be used to design a personalized prosthesis instead of selecting an optimal generic prosthesis.

Figure 7:
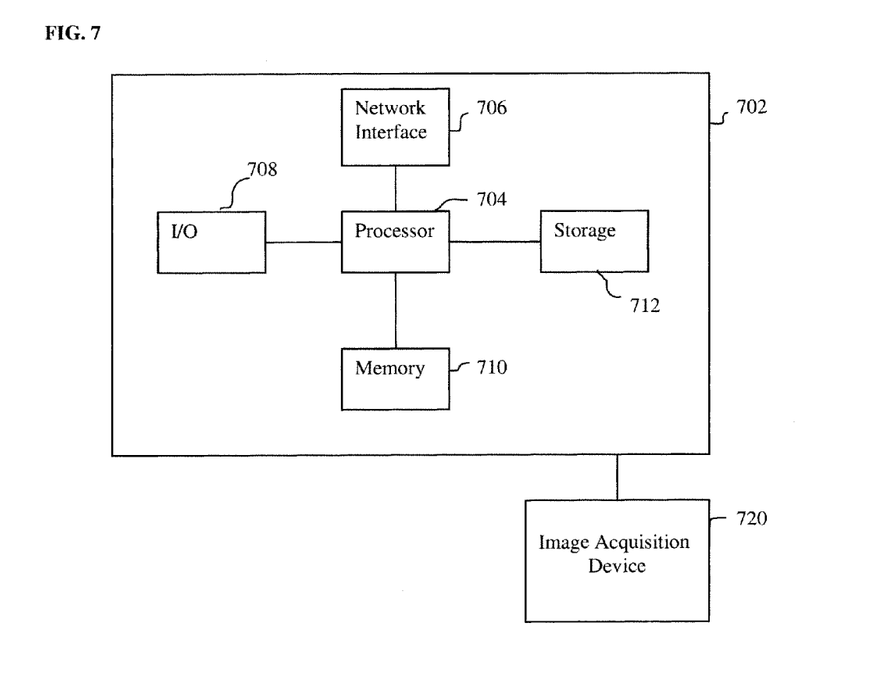
FIG. 7 is a high-level block diagram of a computer capable of implementing the present invention.

The above-described methods for providing organ model based clinical decision support may be implemented on a computer using well-known computer processors, memory units, storage devices, computer software, and other components. A high-level block diagram of such a computer is illustrated in FIG. 7. Computer 702 contains a processor 704, which controls the overall operation of the computer 702 by executing computer program instructions which define such operation. The computer program instructions may be stored in a storage device 712 (e.g., magnetic disk) and loaded into memory 710 when execution of the computer program instructions is desired. Thus, the steps of the method of FIG. 1 may be defined by the computer program instructions stored in the memory 710 and/or storage 712 and controlled by the processor 704 executing the computer program instructions. An image acquisition device 720, such as a CT scanning device, can be connected to the computer 702 to input image data to the computer 702. It is possible to implement the image acquisition device 720 and the computer 702 as one device. It is also possible that the image acquisition device 720 and the computer 702 communicate wirelessly through a network. The computer 702 also includes one or more network interfaces 706 for communicating with other devices via a network. The computer 702 also includes other input/output devices 708 that enable user interaction with the computer 702 (e.g., display, keyboard, mouse, speakers, buttons, etc.). Such input/output devices 708 may be used in conjunction with a set of computer programs as an annotation tool to annotate volumes received from the image acquisition device 720. One skilled in the art will recognize that an implementation of an actual computer could contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for providing medical decision support using virtual organ models, comprising:
   generating a virtual patient-specific organ model from medical image data of a patient; and
   retrieving, from a plurality of previously stored virtual organ models, one or more similar organ models to the patient-specific organ model using a learned discriminative distance function, wherein the learned discriminative distance function is trained based on equivalence constraints assigned to training data.

2. The method of claim 1, wherein the medical image data comprises at least one of a 3D volume or a 4D sequence of medical image data.

3. The method of claim 1, wherein the step retrieving, from a plurality of previously stored virtual organ models, one or more similar organ models to the patient-specific organ model using a learned discriminative distance function, from a plurality of previously stored organ models, one or more similar organ models to the patient-specific organ model using a learned discriminative distance function comprises:
   detecting the one or more similar organ models to the patient-specific organ model using a learned discriminative distance function based on features of the patient-specific organ model, the features including clinical measurements extracted from the patient-specific organ model.

4. The method of claim 1, wherein the patient-specific organ model comprises at least one of an aortic valve model, a mitral valve model, or a pulmonary valve model.

5. The method of claim 1, wherein the learned discriminative distance function is trained based on the equivalence constraints assigned to the training data using one of Random Forests or a boosting algorithm.

6. The method of claim 1, further comprising:
   classifying the patient-specific organ model into one of a first class or a second class based on the retrieved one or more similar organ models to the patient-specific organ model.

7. The method of claim 6, wherein the step of classifying the patient-specific organ model into one of a first class or a second class based on the retrieved one or more similar organ models to the patient-specific organ model comprises:
   clustering the plurality of previously stored organ models into a first cluster corresponding to the first class and a second cluster corresponding to the second class; and assigning the patient-specific organ model to one of the first cluster or the second cluster based on the retrieved one or more similar organ models to the patient-specific organ model.

8. The method of claim 6, wherein the step of classifying the patient-specific organ model into one of a first class or a second class based on the retrieved one or more similar organ models to the patient-specific organ model comprises:
classifying the patient-specific organ model into one of a healthy class or a diseased class based on the retrieved one or more similar organ models to the patient-specific organ model.

9. The method of claim 6, wherein the patient specific organ model comprises a patient-specific pulmonary valve model, and the step of classifying the patient-specific valve model into one of a first class or a second class based on the retrieved one or more similar organ models to the patient-specific organ model comprises:
classifying the patient-specific pulmonary valve model as suitable or non-suitable for percutaneous pulmonary valve implantation (PPVI) based on the retrieved one or more similar organ models.

10. The method of claim 1, wherein the patient-specific organ model represents a diseased organ and the retrieved one or more similar organ models represent a healthy organ corresponding to the diseased organ represented by the patient-specific organ model, the method further comprising:
automatically determining personalized treatment targets for said diseased organ based on the retrieved one or more similar organ models.

11. The method of claim 1, further comprising:
displaying a neighborhood graph visualizing similarities between the patient-specific organ model and the plurality of previously stored organ models based on similarity measures determined using the learned discriminative distance function.

12. An apparatus for providing medical decision support using virtual organ models, comprising:
means for generating a virtual patient-specific organ model from cardiac image data of a patient; and
means for retrieving, from a plurality of previously stored virtual organ models, one or more similar organ models to the patient-specific organ model using a learned discriminative distance function, wherein the learned discriminative distance function is trained based on equivalence constraints assigned to training data.

13. The apparatus of claim 12, wherein the means for retrieving, from a plurality of previously stored virtual organ models, one or more similar organ models to the patient-specific organ model using a learned discriminative distance function comprises:
means for detecting the one or more similar organ models to the patient-specific organ model using a learned discriminative distance function based on features of the patient-specific organ model, the features including clinical measurements extracted from the patient-specific organ model.

14. The apparatus of claim 12, wherein the learned discriminative distance function is trained based on the equivalence constraints assigned to the training data using one of Random Forests or a boosting algorithm.

15. The apparatus of claim 12, further comprising:
means for classifying the patient-specific organ model into one of a first class or a second class based on the retrieved one or more similar organ models to the patient-specific organ model.

16. The apparatus of claim 15, wherein the means for classifying the patient-specific organ model into one of a first class or a second class based on the retrieved one or more similar organ models to the patient-specific organ model comprises:
means for clustering the plurality of previously stored organ models into a first cluster corresponding to the first class and a second cluster corresponding to the second class; and
means for assigning the patient-specific organ model to one of the first cluster or the second cluster based on the retrieved one or more similar organ models to the patient-specific organ model.

17. The apparatus of claim 15, wherein the means for classifying the patient-specific organ model into one of a first class or a second class based on the retrieved one or more similar organ models to the patient-specific organ model comprises:
means for classifying the patient-specific organ model into one of a healthy class or a diseased class based on the retrieved one or more similar organ models to the patient-specific organ model.

18. The apparatus of claim 15, wherein the patient specific organ model comprises a patient-specific pulmonary valve model, and the means for classifying the patient-specific organ model into one of a first class or a second class based on the retrieved one or more similar organ models to the patient-specific organ model comprises:
means for classifying the patient-specific pulmonary valve model as suitable or non-suitable for percutaneous pulmonary valve implantation (PPVI) based on the retrieved one or more similar organ models.

19. The apparatus of claim 12, wherein the patient-specific organ model represents a diseased organ and the retrieved one or more similar organ models represent a healthy organ corresponding to the diseased organ represented by the patient-specific organ model, the apparatus further comprising:
means for automatically determining personalized treatment targets for said diseased organ based on the retrieved one or more similar organ models.

20. The apparatus of claim 12, further comprising:
means for displaying a neighborhood graph visualizing similarities between the patient-specific organ model and the plurality of previously stored organ models based on similarity measures determined using the learned discriminative distance function.

21. A non-transitory computer readable medium encoded with computer executable instructions for providing medical decision support using virtual organ models, the computer executable instructions defining steps comprising:
generating a patient-specific virtual organ model from medical image data of a patient; and
retrieving, from a plurality of previously stored virtual organ models, one or more similar organ models to the patient-specific organ model using a learned discriminative distance function, wherein the learned discriminative distance function is trained based on equivalence constraints assigned to training data.

22. The computer readable medium of claim 21, wherein the computer executable instructions defining the step of retrieving, from a plurality of previously stored virtual organ models, one or more similar organ models to the patient-specific organ model using a learned discriminative distance function comprise computer executable instructions defining the step of:
detecting the one or more similar organ models to the patient-specific organ model using a learned discriminative distance function based on features of the patient-specific organ model, the features including clinical measurements extracted from the patient-specific organ model.

23. The computer readable medium of claim 21, wherein the learned discriminative distance function is trained based on the equivalence constraints assigned to the training data using one of Random Forests or a boosting algorithm.

24. The computer readable medium of claim 21, further comprising computer executable instructions defining the step of:
classifying the patient-specific organ model into one of a first class or a second class based on the retrieved one or more similar organ models to the patient-specific organ model.

25. The computer readable medium of claim 24, wherein the computer executable instructions defining the step of classifying the patient-specific organ model into one of a first class or a second class based on the retrieved one or more similar organ models to the patient-specific organ model comprise computer executable instructions defining the steps of:
clustering the plurality of previously stored organ models into a first cluster corresponding to the first class and a second cluster corresponding to the second class; and
assigning the patient-specific organ model to one of the first cluster or the second cluster based on the retrieved one or more similar organ models to the patient-specific organ model.

26. The computer readable medium of claim 24, wherein the computer executable instructions defining the step of classifying the patient-specific organ model into one of a first class or a second class based on the retrieved one or more similar organ models to the patient-specific organ model comprise computer executable instructions defining the step of:
classifying the patient-specific organ model into one of a healthy class or a diseased class based on the retrieved one or more similar organ models to the patient-specific organ model.

27. The computer readable medium of claim 24, wherein the patient specific organ model comprises a patient-specific pulmonary valve model, and the computer executable instructions defining the step of classifying the patient-specific organ model into one of a first class or a second class based on the retrieved one or more similar organ models to the patient-specific organ model comprise computer executable instructions defining the step of:
classifying the patient-specific pulmonary valve model as suitable or non-suitable for percutaneous pulmonary valve implantation (PPVI) based on the retrieved one or more similar organ models.

28. The computer readable medium of claim 21, wherein the patient-specific organ model represents a diseased organ and the retrieved one or more similar organ models represent a healthy heart valve corresponding to the diseased organ represented by the patient-specific organ model, further comprising computer executable instructions defining the step of:
automatically determining personalized treatment targets for said diseased organ based on the retrieved one or more similar organ models.

29. The computer readable medium of claim 21, further comprising computer executable instructions defining the step of:
displaying a neighborhood graph visualizing similarities between the patient-specific organ model and the plurality of previously stored organ models based on similarity measures determined using the learned discriminative distance function.

* * * * *